(12) United States Patent
Mills et al.

(10) Patent No.: US 10,215,682 B2
(45) Date of Patent: Feb. 26, 2019

(54) METHODS, DEVICE AND APPARATUS FOR EVALUATING ELECTRICAL CURRENT THREAT EFFECTS AT JOINTS

(71) Applicants: AIRBUS OPERATIONS LIMITED, Bristol (GB); AIRBUS GROUP LIMITED, London (GB); AIRBUS OPERATIONS SAS, Toulouse (FR)

(72) Inventors: Richard E. Mills, Bristol (GB); Franck Flourens, Bristol (GB); Matthew Cole, Bristol (GB); Matthew Jenkins, Bristol (GB); Simon Evans, Bristol (GB)

(73) Assignees: AIRBUS OPERATIONS LIMITED, Bristol (GB); AIRBUS GROUP LIMITED, London (GB); AIRBUS OPERATIONS (S.A.S.), Toulouse (FR)

( * ) Notice: Subject to any disclaimer, the term of this patent is extended or adjusted under 35 U.S.C. 154(b) by 626 days.

(21) Appl. No.: 14/826,682

(22) Filed: Aug. 14, 2015

(65) Prior Publication Data
US 2016/0047734 A1 Feb. 18, 2016

(30) Foreign Application Priority Data
Aug. 14, 2014 (GB) .................................. 1414472.9

(51) Int. Cl.
*G01N 15/14* (2006.01)
*G01N 25/00* (2006.01)
(Continued)

(52) U.S. Cl.
CPC ......... *G01N 15/1434* (2013.01); *B64D 45/02* (2013.01); *F16B 37/14* (2013.01);
(Continued)

(58) Field of Classification Search
None
See application file for complete search history.

(56) References Cited

U.S. PATENT DOCUMENTS 4,916,401 A * 4/1990 Bogard .................. G01R 31/00
324/536
8,129,979 B2 3/2012 Lewke
(Continued)

FOREIGN PATENT DOCUMENTS

EP 2385246 A1 11/2011
WO 2013178985 A1 12/2013

OTHER PUBLICATIONS

The European Organisation for Civil Aviation Equipment (EUROCAE); EUROCAE document ED-105 "Aircraft Lightning Test Methods" (Apr. 2005).

*Primary Examiner* — Daniel S Larkin
(74) *Attorney, Agent, or Firm* — Nixon & Vanderhye P.C.

(57) ABSTRACT

A method and device is disclosed for measuring one or more physical properties of, and/or induced by, out-gassing products released from and/or trapped within a joint in response to a lightning strike or other electrical current threat. A device for measuring one or more physical properties of, and/or induced by, gases, plasma and/or particles released from a joint in response to an electrical current threat. The joint includes a fastener passing through a structure so that an end of the fastener protrudes from the structure. The device includes a containment member having a base surrounding an opening into a cavity, the containment member being arranged to be mounted over the end of the fastener to enclose the end of the fastener within the cavity and to seal the opening; and one or more sensors arranged to measure physical properties of gases, plasma and/or particles contained by the cavity.

12 Claims, 8 Drawing Sheets

(51) Int. Cl.
   *G01N 27/00*   (2006.01)
   *B64D 45/02*   (2006.01)
   *F16B 37/14*   (2006.01)
   *G01N 27/92*   (2006.01)
   *F16B 33/00*   (2006.01)

(52) U.S. Cl.
   CPC ............ *G01N 25/00* (2013.01); *G01N 27/00* (2013.01); *G01N 27/92* (2013.01); *F16B 33/004* (2013.01)

(56) References Cited

U.S. PATENT DOCUMENTS

| | | | |
|---|---|---|---|
| 2007/0258090 A1* | 11/2007 | Kwon | G01J 3/443 |
| | | | 356/328 |
| 2011/0181393 A1* | 7/2011 | Tillotson | H04Q 9/00 |
| | | | 340/10.1 |
| 2011/0273161 A1 | 11/2011 | Lewke | |
| 2015/0184688 A1 | 7/2015 | Dobbin et al. | |

* cited by examiner

METHODS, DEVICE AND APPARATUS FOR EVALUATING ELECTRICAL CURRENT THREAT EFFECTS AT JOINTS

RELATED APPLICATIONS

The present application claims priority from Great Britain Application Number 1414472.9, filed Aug. 14, 2014, the disclosure of which is hereby incorporated by reference herein in its entirety.

FIELD OF THE INVENTION

The present invention relates to methods and equipment for evaluating the effects of lightning strikes or other electrical current threats at structural joints. In particular, it relates to methods and equipment for analysing the physical properties of, or induced by, gases, plasma and/or particles released from a joint in response to an electrical current threat, and for determining a set of design rules for joints subject to such a threat.

BACKGROUND OF THE INVENTION

Aircraft are typically required to fly in weather conditions in which the airframe structure may be subjected to lightning strikes. Such lightning strikes often attach to the aircraft at a fastener of a fastened joint, or are conducted via aircraft structure to such a fastener. It is necessary to predict and control the effects of such lightning strikes, particularly at fuel tank joints, in order to prevent fuel ignition.

FIG. 1 is a side view of part of a fastener assembly passing through a panel 1, which may be a composite or metallic panel. The assembly comprises a fastener comprising an externally threaded bolt 2, an internally threaded nut 3, and a washer 4 (the fastener may alternatively comprise any other known fastener type, such as a rivet or swage fastener). In the event of a lightning strike hitting the panel 1 and current flowing through the fastener, sparking at the joint (e.g. at the interface between the panel 1 and the fastener) may cause localised pressure build up and ejection of a shower of sparks from the fastener. The pressure build up may also cause gases, plasma and hot particles to be released from the joint.

Typical locations of such out-gassing are indicated by reference 5 in FIG. 1. The panel 1 may provide a fuel tank boundary and the fastener may therefore be immersed in fuel or fuel vapour. A lightning strike at the fastener may thus provide sparking and hot gas ignition sources which could cause ignition of the fuel vapour. Other electrical current threats, such as threats from electrical equipment on the aircraft, may also provide such ignition sources.

In some cases the pressure build up may be sufficiently high to cause structural damage to the panel 1. Where the panel is made from a composite material, the pressure may cause delamination as the gas, plasma and/or particles try to escape from the joint.

Previous testing methods used in the aerospace industry to detect fuel ignition sources during simulated lightning strike tests are based upon photography and/or flammable gas techniques, as defined in EUROCAE ED-105, Section 7.7 and equivalent SAE and MIL-STD standard documents. Such techniques provide a discrete pass/fail result, without any quantitative information about the characteristics of the out-gassing event and associated margins. There are no known methods or devices for measuring physical properties of the gases, plasma and/or particles released during an out-gassing event.

In fact, there are still several unknowns about the physical mechanisms at work during an out-gassing event. There is therefore a need for a device and methods for creating improved data about such out-gassing events. There is also a need to better understand the influence of design features of the joint on the degree of out-gassing.

SUMMARY OF THE INVENTION

A first aspect of the invention provides a device for measuring one or more physical properties of, and/or induced by, gases, plasma and/or particles released from a joint in response to an electrical current threat, the joint comprising a fastener passing through a structure so that an end of the fastener protrudes from the structure, the device comprising:

a containment member having a base surrounding an opening into a cavity, the containment member being arranged to be mounted over the end of the fastener to enclose the end of the fastener within the cavity and to seal the opening; and one or more sensors arranged to measure: one or more physical properties of gases, plasma and/or particles contained by the cavity; and/or one or more physical properties of the containment member or joint induced by gases, plasma and/or particles contained by the cavity.

The device according to the first aspect can be used to obtain valuable data about the products of out-gassing events caused by lightning strikes or other electrical current threats. For example, the device may be used in test programmes in which lightning strikes at a joint are simulated, in order to obtain information about the physical properties of, or caused by, out-gassing products (gases, plasma and/or particles ejected from the joint in response to the lightning strike). Such information enables the physics of out-gassing events to be better understood, and the likely outcomes of a lightning strike at a joint to be better predicted.

Using known testing techniques, with little information available about the physics of out-gassing events, it is difficult to predict the effect of a lightning strike on the integrity of a joint. As such, new joint designs must be subject to a test campaign to determine whether they are sufficiently protected against lightning strike. Such test campaigns are expensive and contribute to delays in the design process. The known testing techniques provide a simple discrete pass/fail result. EUROCAE ED-105, Section 7.7 describes suitable photographic and flammable gas techniques, which indicate whether an ignition source is present or not. Thus, known test campaigns are blunt instruments, in the sense that they can only be used to determine whether a joint passes or fails the test, and cannot provide information as to whether the joint is over-engineered. Such tests also cannot currently be used to provide data with which to predict the outcome of tests on similar joints.

In contrast, the device of the first aspect can provide data about the physical properties of out-gassing products and their effects on surrounding structure which can be used to inform the joint design process. The size of test campaigns will be much reduced, and over-engineering of joints can be avoided.

A known method of protection at joints at which out-gassing products or sparks caused by an electrical current threat such as a lightning strike may pose an ignition risk (e.g. at aircraft fuel tank joints) is to enclose the protruding fastener end within the sealed cavity of a cap (also known as a nut cap or spark suppression cap). The device of the first aspect may be used to simulate such a cap, with the cavity of the containment member corresponding in size, shape, or other characteristics to the cavity of the cap. The device may thus serve to provide information about the design requirements for such caps.

The physical properties of the contained out-gassing products (gases, plasma and/or particles) may include any measurable, or observable, property of the products whose value describes a state of those products. Similarly, the physical properties induced by the out-gassing products may include any measurable, or observable, property of the containment member or joint that is induced (caused) by the contained out-gassing products and whose value describes a state of the containment member or joint.

The one or more sensors of the device of the first aspect may comprise: a pressure sensor in fluid communication with the cavity and arranged to measure a pressure within the cavity; a temperature gauge arranged to measure a temperature or temperature distribution of the containment member (a temperature or temperature distribution of a body of the containment member, or a temperature or temperature distribution within the cavity) or joint (a temperature or temperature distribution within the structure and/or the fastener); and/or a light sensor arranged to measure a light emitted within the cavity (this may include measuring a spectral analysis of the light).

The pressure sensor may provide data about the pressure of the contained out-gassing products (gases, plasma and/or particles) which is used to inform the design process. For example, the measured pressure may serve to determine the pressure which must be withstood by a cap (e.g. nut cap or spark suppression cap) intended to enclose the protruding fastener end of the joint. Similarly, the temperature or temperature distribution data may be used to inform material selection. The light sensor may detect any spark generated at the joint during the out-gassing event. Moreover, the light sensor may perform a spectral analysis in order to provide additional information regarding the properties of the out-gassing products.

The one or more sensors may comprise a fibre optic sensor. Such sensors are compact, and resistant to electrical interference.

A second aspect of the invention provides apparatus for measuring one or more physical properties of, and/or induced by, gases, plasma and/or particles released from a joint in response to an electrical current threat, the apparatus comprising:

a joint comprising a fastener passing through a structure so that an end of the fastener protrudes from the structure;

a device according to the first aspect; and means for delivering an electrical current representative of the electrical current threat to the fastener, wherein the containment member of the device is installed over the end of the fastener so as to enclose the end of the fastener within the cavity and to seal the opening.

The second aspect thus provides apparatus with which to use the device of the first aspect to measure physical properties of the out-gassing products of a simulated lightning strike or other electrical current threat, or the physical properties induced in the joint or containment member by such products. Other electrical current threats may include currents from malfunctioning electrical equipment.

The means for delivering an electrical current representative of the electrical current threat (e.g. lightning strike) may comprise any device or apparatus suitable for delivering a representative current, such as a high-current waveform as defined in EUROCAE ED-105, or equivalent standard document. It may comprise a high voltage generator, laser or any other suitable device. The means for delivering an electrical current may be arranged to deliver the representative current directly to the fastener (to simulate e.g. a direct lightning attachment), or to a point on the structure from where the delivered current will be conducted to the fastener (to simulate e.g. a conducted current threat from a lightning strike). The apparatus may be used to measure the effects on the out-gassing products of the fastener of either current delivery scenario.

The structure of the joint may comprise one or more panels attached to a sub-frame member, such as a sub-frame member representative of a rib, stringer, frame, spar, or other structural member, by the fastener. In some embodiments the joint may comprise two sub-frame members attached to one another by the fastener. The opening of the containment member may be sealed by a sealed contact with the structure. For example, the containment member may be attached to the structure via a bead of adhesive or sealing material extending around the opening.

The joint may comprise a plurality of fasteners passing through the structure, and the representative current may be delivered to one or more of the plurality of fasteners. The apparatus may comprise a plurality of devices according to the first aspect.

The apparatus may comprise a recording device arranged to record changes in the measured one or more physical properties over time. Thus, the changes in the one or more physical properties following the application of the representative current may be tracked. It is expected that at least some physical properties, such as pressure, temperature and light, may rise to a peak following the application of the representative current, and then start to fall. Information about the timing of such peaks, and the gradient of the rise and fall, may be useful for informing the design process.

The joint preferably comprises a test assembly representative of a joint of an aircraft fuel tank. Such a test assembly typically comprises one or more composite or metallic panels attached to a composite or metallic sub-frame member, such as a rib, stringer, frame, spar, or other fuel tank structural member, by the fastener. The test assembly may alternatively comprise two composite or metallic sub-frame members fastened to one another by the fastener. Thus, the aircraft fuel tank joint may be a joint at the fuel tank boundary, or a joint within the fuel tank.

A third aspect of the invention provides a method of measuring one or more physical properties of, and/or induced by, gases, plasma and/or particles released from a joint in response to an electrical current threat, the joint comprising a fastener passing through a structure so that an end of the fastener protrudes from the structure, the method including the steps of:

enclosing the end of the fastener within a sealed cavity;

delivering an electrical current representative of the electrical current threat to the fastener; and measuring: one or more physical properties of gases, plasma and/or particles released from the joint in response to the applied current and contained within the sealed cavity; and/or one or more physical properties of the containment member or joint induced by the gases, plasma and/or particles.

The method of the third aspect may be put into effect using the device of the first aspect or the apparatus of the second aspect. The benefits and advantages of the first and second aspects discussed above are equally applicable to the method of the third aspect. In particular, the method of the third aspect can be used to obtain valuable data about the products of out-gassing events caused by lightning strikes or other electrical current threats. For example, the method may be used in test programmes in which lightning strikes at the joint are simulated, in order to obtain information about the physical properties of, or caused by, out-gassing products (gases, plasma and/or particles ejected from the joint in response to the lightning strike). Such information enables the physics of out-gassing events to be better understood, and the likely outcomes of a lightning strike at a joint to be better predicted.

Known testing techniques used to determine whether a joint may provide an ignition source in the event of a lightning strike provide a simple discrete pass/fail result. EUROCAE ED-105, Section 7.7 describes suitable photographic and flammable gas techniques, which indicate whether an ignition source is present or not. These techniques thus provide no measurement of physical properties of, or induced by, out-gassing products, but instead only detect the presence of an ignition source such as a spark.

The measuring step of the third aspect may include measuring changes in the one or more physical properties over time. Thus, the changes in the one or more physical properties following the application of the representative current may be tracked. It is expected that many physical properties, such as pressure, temperature and light, may rise to a peak following the application of the representative current, and then start to fall. Information about the timing of such peaks, and the gradient of the rise and fall, may be useful for informing the design process.

The one or more physical properties may include: a pressure within the sealed cavity (caused by the build-up of out-gassing products in the cavity); a temperature or temperature distribution of the containment member (including the body of the containment member and/or the cavity and its contents) or joint (including the structure and/or fastener); properties of a light emitted within the sealed cavity (e.g. by a spark); and/or a material distribution of gases, plasma and/or particles contained within the sealed cavity. The material distribution of the out-gassing products may comprise information about which materials are present, and in what proportions. Such information may be obtained using spectrograph techniques.

The joint preferably comprises a test assembly representative of a joint of an aircraft fuel tank. In some embodiments the sealed cavity is representative of a sealed cavity of a cap enclosing an end of a fastener at the joint of the aircraft fuel tank. Such a cap may comprise a nut cap, spark suppression cap, or any other cap arranged to contain sparks and/or other out-gassing products in the event of a lightning strike or other electrical current threat experienced at the joint.

A fourth aspect of the invention provides a device for measuring one or more physical properties of, or induced by, gases, plasma and/or particles generated at a joint in response to an electrical current threat, the joint comprising a fastener passing through a structure so that an end of the fastener protrudes from the structure, the device comprising: one or more sensors embedded in the joint and arranged to measure the one or more physical properties, the one or more sensors each comprising a fibre optic sensor.

Such a device can provide information about the nature of, and effect of, generated products contained within the joint. That is, products (gases, plasma and/or particles) that are generated in response to the electrical current threat (e.g. lightning strike), but are trapped within the joint, rather than being released from the joint as part of an out-gassing event. Such trapped generated products will have physical properties which may cause a change in physical properties of the joint. For example, a build-up of trapped generated products within the joint will cause an increase in pressure and temperature, which may in turn cause a change in temperature of the structure and fastener, and flexing of those parts, possibly leading to structural damage. Also, trapped generated products may have an effect only within the joint, with no observable result outside the joint; an example is a spark that is contained wholly within the joint. The device of the fourth aspect can be used to measure such physical properties. In particular, the device can be used to determine the torque to be applied to a fastener of a given assembly in order to contain the pressure within the joint and thereby prevent an out-gassing event. This preload can therefore be specified as one layer of protection against an ignition source.

A fibre optic sensor (or optical fibre sensor) may comprise a sensor that uses optical fibre either as the sensing element (known as an intrinsic sensor), or as a means of relaying signals from a remote sensor to external signal processing equipment (known as an extrinsic sensor). Fibre optic sensors are particularly advantageous because they are sufficiently small and compact to integrate into the joint without requiring significant modification to the joint. For example, an optical fibre may be sandwiched between plies in a composite part, or inserted into a channel in part of the fastener. In addition, no electrical power is needed at the remote sensing location, and fibre optic sensors do not suffer from electrical interference.

A fibre optic sensor may comprise a fibre Bragg grating arranged to measure one of the one or more physical properties. A fibre Bragg grating is a type of distributed Bragg reflector located in a segment of optical fibre. The fibre Bragg grating reflects some wavelengths of light and transmits all others. The reflected wavelengths are sensitive to both strain and temperature, enabling fibre Bragg sensors to directly measure these physical properties. Fibre Bragg gratings can also be modified by the addition of absorbent coatings, for example, to sense the presence of a particular gas, or to measure pressure. Fibre Bragg gratings are particularly suitable for the present application because they are less sensitive to vibration, heat and electromagnetic fields than transitional electronic gauges, and are therefore more reliable when used in the harsh environment of a joint subjected to a (simulated) lightning strike or other electrical current threat. Alternatively, a fibre optic sensor may comprise a Fabry-Perot interferometric sensor. Other fibre optic sensors may comprise a plain optical fibre for performing light spectral analysis.

Each fibre optic sensor is preferably arranged to measure a pressure, temperature, temperature distribution or light emission at the joint. The sensor may be arranged to take such measurements at a particular interface between parts of the joint, for example at a gap between the shank of the fastener and the internal bore of the fastener hole through the structure.

A fifth aspect of the invention provides a method of providing a set of design rules for designing a joint with substantially no ignition threat in response to an electrical current threat, the method including the steps of:

(i) for each of a plurality of joints, each joint comprising a fastener passing through a structure so that an end of the fastener protrudes from the structure, and each joint having a design feature that is different to a corresponding design feature of the other of the plurality of joints:

delivering a current representative of the electrical current threat to the fastener; and measuring one or more physical properties of, or induced by, gases, plasma and/or particles generated at the joint in response to the applied current;

(ii) using the measured physical properties to select one or more joints from the plurality of joints that provide substantially no lightning strike ignition threat; and (iii) determining a set of design rules based on the design features of the selected joints.

The method may alternatively be a method of providing a set of design rules for designing a joint with protection against unacceptable damage due to lightning strike. That is, protection against damage which may pose an unacceptable threat to the integrity of the joint.

The joint is preferably a joint located in a fuel vapour zone, such as a joint of an aircraft fuel tank. That is, the set of design rules is preferably for designing such a joint.

As discussed above, previous devices and methods for analysing the effect of a lightning strike or other electrical current threat on a joint do not provide any information about the physical properties of any out-gassing products or trapped generated products, or their effect on the surrounding joint. Thus, each new joint design must be subjected to a test campaign in which representative test pieces are manufactured and subjected to a representative current. Such test campaigns are expensive and time-consuming, and contribute significantly to the length of the design process. In contrast, the present inventors have developed the method of the fifth aspect in order to provide a test programme which provides a set of design rules for the design of future joints.

The design feature may comprise any feature of a joint that is capable of being modified in order to modify functional characteristics or performance of the joint. For example, the design feature may comprise a thickness or material type of the structure, a size or material type of the fastener, a fastening torque applied to the fastener, or a clearance between the fastener shank and the bore of the fastener hole through the structure. In designing such features, designers will have to work within design rules concerning requirements such as the loads to be carried by the joint, the manufacturing capabilities etc. Previously, requirements concerning protection against lightning strike and other electrical current threats have been provided in terms of the properties of the current threat itself, whereas the method of the fifth aspect provides a set of design rules for design features which will ensure that the resulting joint is protected against such a threat. The design rules provide allowable design margins for that particular design feature.

The set of design rules may be compiled using the data from the design features of the selected joints, and from data extrapolated from that data.

It is likely that several design features will have mutual interdependencies, to the extent that modifying one will lead to a change in the design rules (allowable design margins) for another design feature. Thus, the design rules may be compiled together into a model which reflects those interdependencies.

For each of the plurality of joints the measuring step preferably includes measuring changes in the one or more physical properties over time. Thus, the changes in the one or more physical properties following the application of the representative current may be tracked. It is expected that many physical properties, such as pressure, temperature and light, may rise to a peak following the application of the representative current, and then start to fall. Information about the timing of such peaks, and the gradient of the rise and fall, may be useful for informing the design process.

In some embodiments, for each of the plurality of joints the measuring step includes measuring one or more physical properties of, or induced by, gases, plasma and/or particles released from the joint. That is, the measurement is carried out outside the joint, by measuring the nature or effects of out-gassing products that are ejected from the joint in response to the delivered representative current. A suitable measurement device or apparatus is that of the first or second aspects, and a suitable measurement method is that of the third aspect.

In yet further embodiments, for each of the plurality of joints the measuring step includes measuring one or more physical properties of, or induced by, gases, plasma and/or particles contained within the joint. That is, the measurement is carried out within the joint, by measuring the nature or effects of generated products that are trapped within the joint following delivery of the representative current. A suitable measurement device is that of the fourth aspect.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
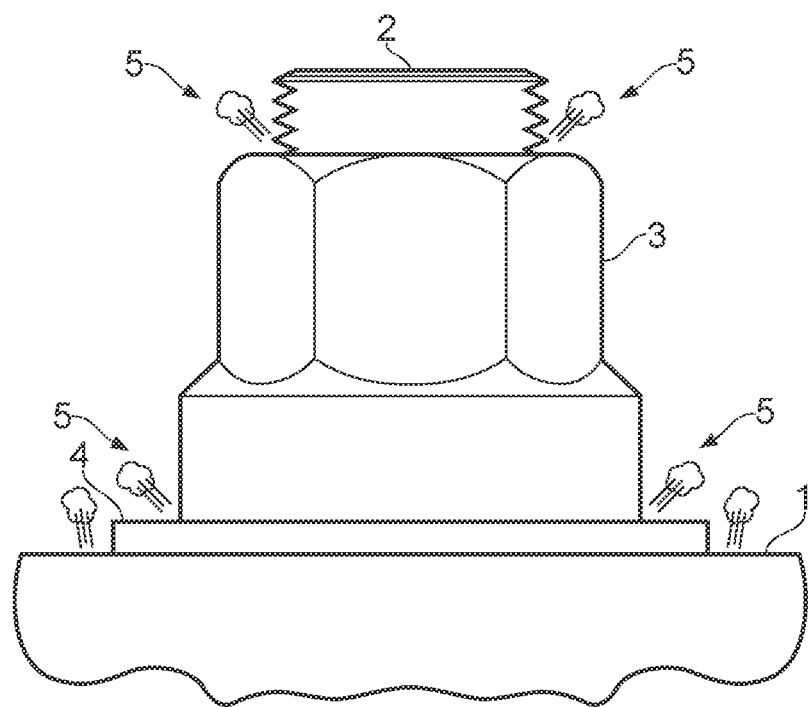
FIG. 1 illustrates possible out-gassing locations at a typical prior art joint.
Figure 2:
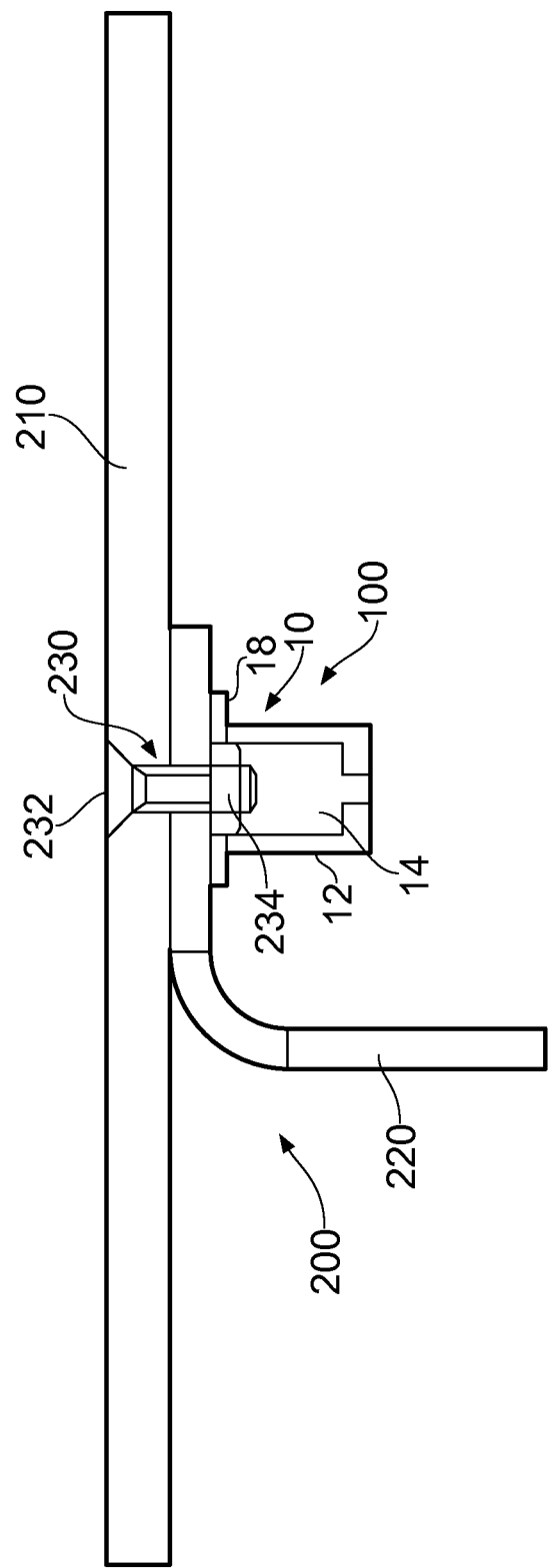
FIG. 2 shows a measurement device according to an embodiment of the invention installed at a joint.
Figure 3A:
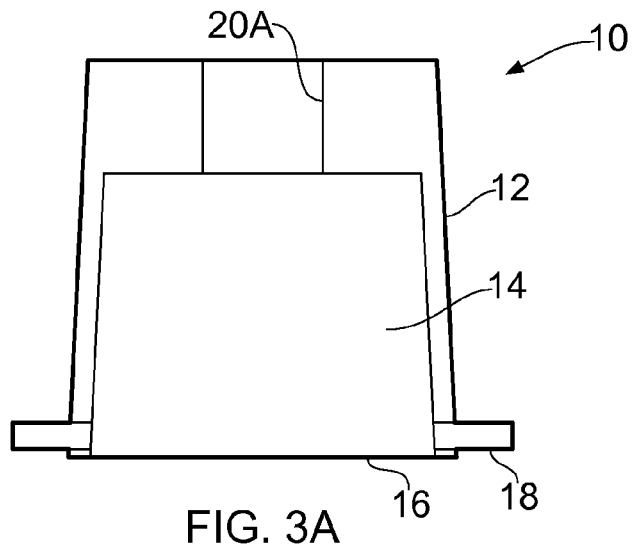
FIGS. 3A-3C show a longitudinal cross-sectional view, and isometric views from above and below, respectively, of a containment member of a measurement device according to an embodiment of the invention.
Figure 3B:
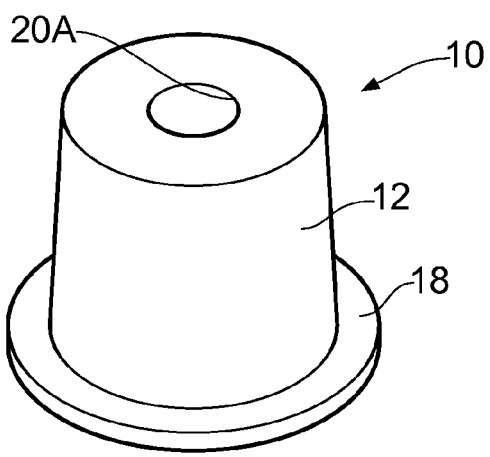
Figure 3C:
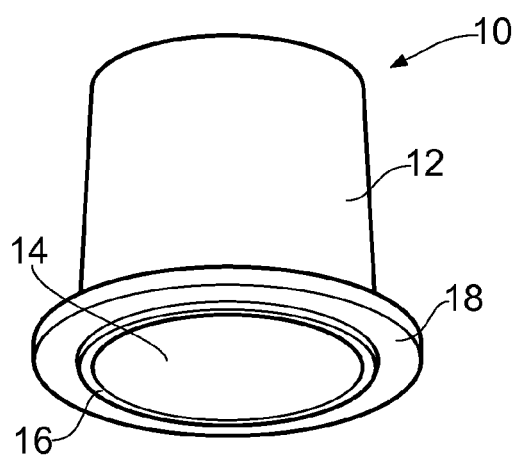
Figure 4:
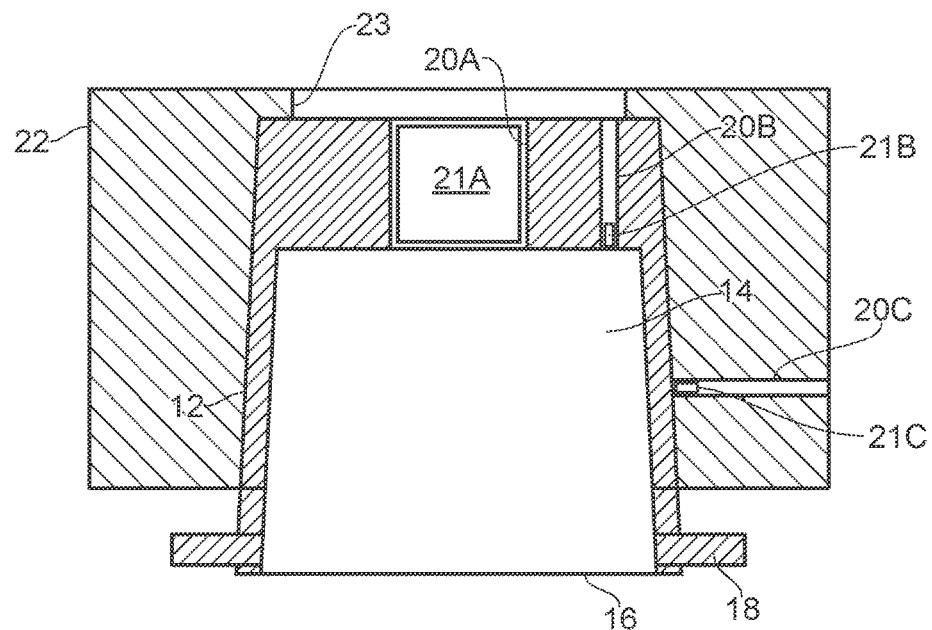
FIG. 4 shows a longitudinal cross-sectional view of a containment member of a measurement device according to an embodiment of the invention assembled with a sensor mount.
Figure 5:
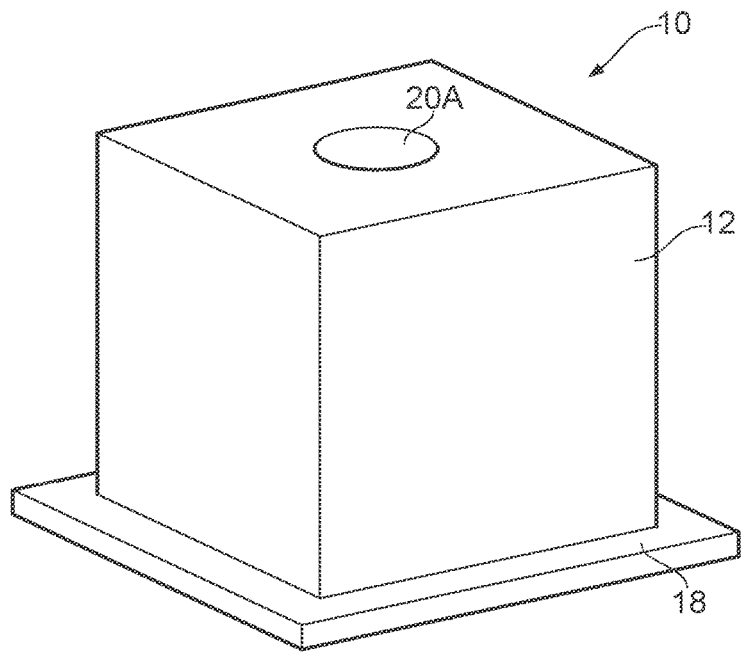
FIG. 5 shows an isometric view of an alternative containment member of a measurement device according to an embodiment of the invention.
Figure 6:
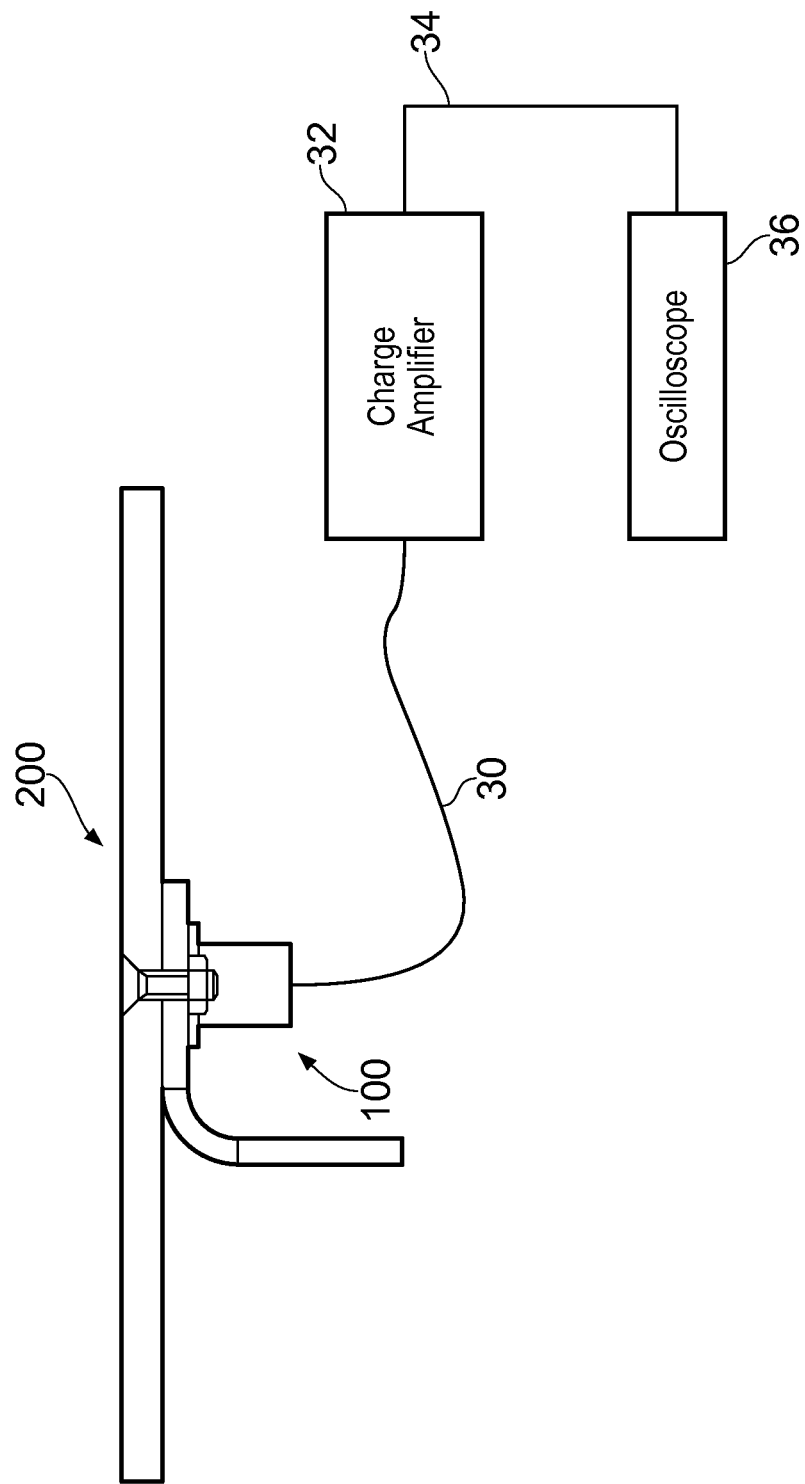
FIG. 6 shows a schematic view of a measurement apparatus according to an embodiment of the invention, including the measurement device of FIGS. 2 to 5 installed at a joint.

Various embodiments of a measurement device 100 according to the invention for measuring physical properties of out-gassing products emitted from a joint 200, and induced effects of such products, are illustrated in FIGS. 2 to 6. FIG. 2 shows the device 100 installed at the joint 200, FIGS. 3-5 show various embodiments of aspects of the device 100, and FIG. 6 shows the device 100 installed at the joint 200 as part of a measurement apparatus.

The joint 200 comprises a panel 210 fastened to a stiffening member 220 by a fastener 230. In the present embodiments the panel 210 is a test piece representative of an aircraft wing surface which provides a fuel tank boundary, and the stiffening member 220 is a test piece representative of an aircraft rib, stringer, spar or other stiffening member within the fuel tank. In other embodiments the joint 200 may be any type of joint between two structural parts of an assembly. The fastener 230 comprises a countersunk bolt 232 and a correspondingly threaded nut 234. In some embodiments the fastener 230 may also include a washer (not shown) between the nut 234 and the stiffening member 220, or may alternatively comprise a raised-head bolt, rivet or other type of fastener. The fastener 230 is typically metallic, e.g. titanium. The panel 210 and stiffening member 220 may be metallic or composite parts. In embodiments in which the panel 210 and stiffening member 220 are composite parts, the parts may be formed from layers of orientated fibres, e.g. glass or carbon fibres, embedded within a resin matrix.

The device 100 includes a containment member 10 which comprises a generally cup-shaped (concave) body 12 having an opening 16 which provides an entrance to a cavity 14 enclosed within the body 12. In the embodiment of FIGS. 3-4 the opening 16 is circular, as is the cross-sectional shape of the body 12, while in the embodiment of FIG. 5 the opening (not shown) and the cross-sectional shape of the body 12 are square. In practice, any shaped opening 16 or body 12 cross-sectional shape will suffice. A continuous flange 18 surrounds the opening 16 and projects radially outwardly from a central axis of the containment member 10.

The containment member 10 is formed from a dielectric material, e.g. a polymer such as Nylon. The material may be semi-translucent so that some light may be transmitted from the cavity 14, through the walls of the containment member.

In use, the containment member 10 is installed over the nut 234 (i.e. the tail end of the fastener) so that the part of the fastener 230 that protrudes from the stiffening member 220 is enclosed within the cavity 14. The flange 18 provides a surface for bonding the containment member 10 to the surface of the stiffening member 220 surrounding the nut 234, and the adhesive or sealing material provides a seal around the opening 16 to thereby seal the cavity 14. Alternatively, the containment member 10 may be installed over the head of the bolt 232.

The containment member 10 includes one or more measurement channels 20A, 20B, 20C within which a sensor can be inserted. In the embodiments, the one or more measurement channels 20A, 20B, 20C include a pressure sensor channel 20A, which extends through an end face of the body 12 along a central axis of the containment member 10. The pressure sensor channel 20A comprises an internally threaded portion (not shown) which enables a suitably sized pressure sensor 21A having an externally threaded portion (not shown) to be inserted into, and interconnected with, the pressure sensor channel 20A. Since the pressure sensor channel 20A extends through the body 12, the pressure sensor 21A will be in fluid communication with the contents of the cavity 14, so that it can measure a pressure of those contents.

In the embodiment of FIG. 4 the one or more measurement channels 20A, 20B, 20C also includes a cavity sensor channel 20B which, like the pressure sensor channel 20A, extends through the end face of the body 12. Thus, a sensor 21B inserted through the cavity sensor channel 20B is in fluid communication with the contents of the cavity 14 in order to be able to measure a physical property of those contents. The sensor 21B will typically comprise a fibre optic sensor, such as an optical fibre, optionally with a fibre Bragg grating, or Fabry-Perot interferometric sensor. The fibre optic sensor can be arranged to measure any desired physical property of the contents of the cavity 14, such as pressure (in embodiments without the pressure sensor channel 20A), temperature, light emission/spectrum, or material properties.

The embodiment of FIG. 4 also includes a removable sensor mount 22, which comprises a generally cup-shaped (concave) body arranged to fit over the body 12 of the containment member 10. The sensor mount 22 includes a central aperture 23 in an end face which provides clearance for a pressure sensor 21A located in the pressure sensor channel 20A, and also includes a body sensor channel 20C of the one or more measurement channels 20A, 20B, 20C. The body sensor channel 20C extends through a side wall of the sensor mount 22 so that an end of the body sensor channel 20C abuts a side wall of the body 12 of the containment member 10. Thus, a sensor 21C inserted through the body sensor channel 20C can measure a physical property of the body 12, and in particular a change in such a physical property caused by contents of the cavity 14. The sensor 21C will typically comprise a fibre optic sensor or a thermocouple. The sensor 21C can be arranged to measure any desired physical property of the body 12, such as temperature or deflection (bending) of the body 12. In embodiments in which the containment member 10 is translucent or semi-translucent, a fibre optic sensor within the body sensor channel 20C may be arranged to perform light emission and/or light spectrum measurements. In embodiments in which the containment member 10 is a semi-translucent, the fibre optic sensor within the body sensor channel 20C may be arranged to perform light emission and/or light spectrum measurements.

In other embodiments the measurement channels 20A, 20B, 20C may be arranged in any appropriate location, in order to measure any desired property of the cavity 14 contents, body 12, or structure 210, 220 resulting from a release of out-gassing products (gases, plasma and/or particles) into the cavity 14 following a simulated lightning strike.

In the illustrated embodiments the pressure sensor 21A mounted in the pressure sensor channel 20A comprises a piezoelectric pressure sensor device. To monitor and record measurements from the pressure sensor 21A, the sensor 21A is connected via a cable 30 to a charge amplifier 32, as shown in FIG. 6. The charge amplifier 32 converts the change in electrical charge that is detected by the pressure sensor 21A to a change in voltage. The charge amplifier 32 is connected via a cable 34 to an oscilloscope 36, which captures and records the measured voltage. Calibration factors are then used to convert the voltage measurement to a pressure measurement.

Measurements obtained from other sensors 21B 21C, such as optical fibre sensors, mounted in the measurement channels 20B, 20C may be monitored and recorded via an appropriate set-up, as the skilled person will readily understand, the use of known equipment to capture and record data from known sensors being well understood in the art.

The measurement apparatus may also include an externally-mounted thermal camera (not shown) for monitoring the temperature distribution at the visible surfaces of the containment member 10 and joint 200, and the changes of such temperature distributions over time.

In use, the measurement device 100 is positioned so that the part of the fastener 230 that protrudes from the stiffening member 220 is enclosed within the cavity 14, and the flange 18 is bonded to the surface of the stiffening member 220 to seal the cavity 14. The one or more sensors 21A, 21B, 21C are then installed in their respective measurement channels 20A, 20B, 20C and connected to their respective monitoring and recording devices. In other embodiments a countersunk head of the fastener 230 may be enclosed by the cavity 14.

The joint 200 is then subjected to one or more simulated lightning strikes. The simulated lightning strike may comprise a simulated direct attachment in which a current representative of a lightning strike is applied directly to the bolt 232 head of the fastener 230 (i.e. the exposed part of the fastener 230 at the exterior surface of the panel 210) or a simulated conducted current in which a current representative of a lightning strike is applied elsewhere within the joint 200, and the current is conducted through the joint 200 to the fastener 230. The appropriate peak current for the representative current depends on the location of the fastener 230 (e.g. its location on the aircraft). The current may also be altered to simulate a range of threat levels to evaluate trends and thresholds. In some embodiments the joint 200 is instead subjected to an electrical current representative of an electrical current threat other than a lightning strike. Such a threat may be, e.g. posed by an electrical short circuit between an electrical system and surrounding aircraft structure. The characteristics of such an electrical current threat will be different to that of a lightning strike.

In the event of the simulated lightning strike (or other representative electrical current) causing an out-gassing event at the fastener 230, any out-gassing products (gas, plasma and/or particles) ejected from the joint are contained by the cavity 14 of the measurement device 100. The sensors 21A, 21B, 21C measure physical properties of the out-gassing products or the effect of such products on the joint 200 or containment member 10. For example, a pressure sensor within the pressure sensor channel 20A may measure a pressure of the contained out-gassing products, including a change in that pressure over time, a fibre optic sensor within the cavity sensor channel 20A may measure the electromagnetic spectrum of light emitted within the cavity to characterise the chemistry of any products generated by the out-gassing event and expelled from the joint, and a thermocouple within the body sensor channel 20C may measure a temperature of the body 12 of the containment member 10, including a change in that temperature over time.

Further data may also be gathered from an external thermal camera monitoring the joint, and by using spectrograph techniques to determine a material distribution of the contained out-gassing products.

The measured data from the sensors 21A, 21B, 21C, and optional additional data, may then be used to analyse the physical processes at work during the out-gassing event. Alternatively, or in addition, the measured data may be used to determine whether the joint provides an acceptable fuel ignition threat. This information may be used to inform the design of future joints, as discussed further below.

Two embodiments of a measurement device according to the invention for measuring physical properties of products (plasma, gases and/or particles) generated in response to a simulated lightning strike and contained within a joint 200, and induced effects of such generated products, are illustrated in FIGS. 7, 8 and 9A-C. Features of these embodiments that are shared with the embodiments of FIGS. 2 to 6 are identified using the same reference numerals, and will not be described again here.

Figure 7:
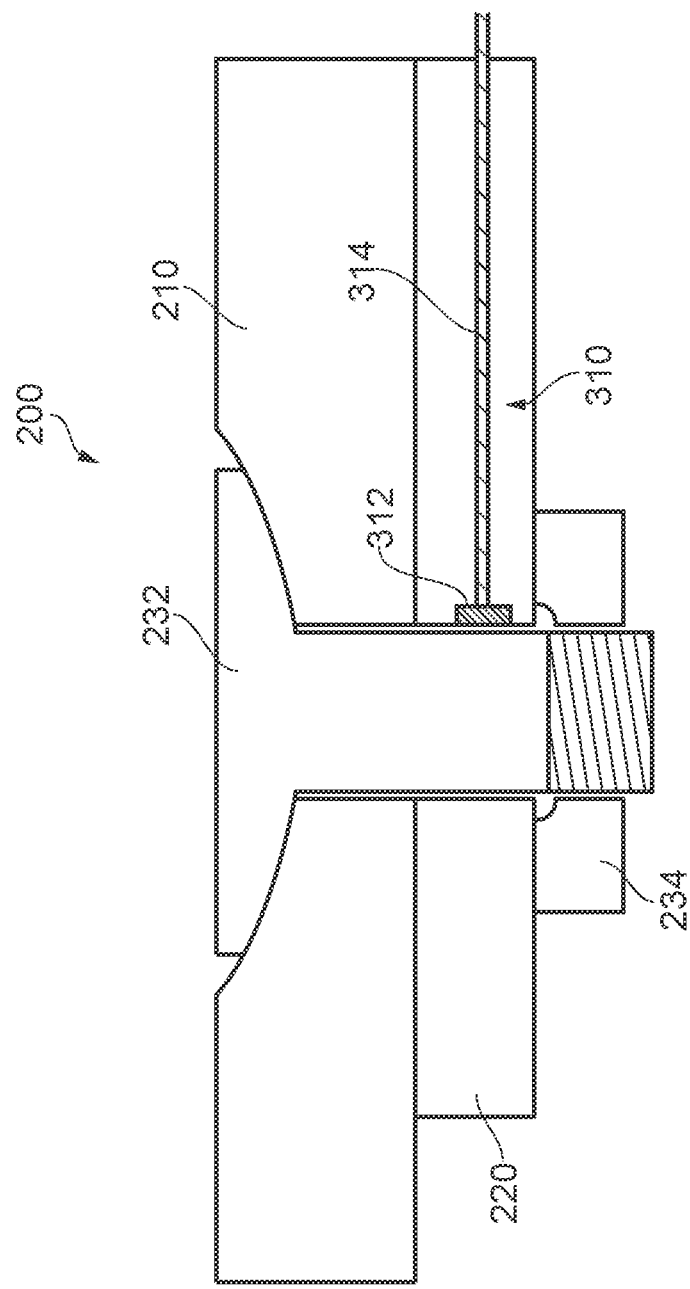
FIG. 7 shows a cross-sectional view of an optical fibre sensor measurement device according to an embodiment of the invention.

The embodiment of FIG. 7 shows a fibre optic sensor 310 embedded within the stiffening member 220. In other embodiments the fibre optic sensor 310 may be embedded within the panel 210. The fibre optic sensor 310 comprises a sensor head 312 which provides the sensing element for measuring a desired physical property at the sensor head 312 location. In this embodiment the sensor head 312 is located at the interface between the bolt 232 shank and the fastener bore through the stiffening member 220. The sensor head 312 may be located at any other location within the joint where information about the physical properties of trapped generated products, or the physical properties of the joint which are affected by such trapped products, is desired. The fibre optic sensor 310 also comprises an optical fibre 314 to transmit measurement data from the sensor head 312.

The sensor head 312 may comprise a fibre Bragg grating, or any other suitable sensing element. It can be arranged to measure any desired physical property, such as the pressure, temperature, light emission or material properties of trapped generated products, or the temperature or deflection (i.e. bending) of any part of the joint caused by such products. A fibre optic sensor 310 is particularly advantageous in this embodiment, and the embodiment of FIGS. 8 and 9, described below, because they are sufficiently small and compact to integrate into the joint without requiring significant modification to the joint. In addition, no electrical power is needed at the remote sensing location of the sensor head 312, and fibre optic sensors do not suffer from electrical interference.

Figure 8:
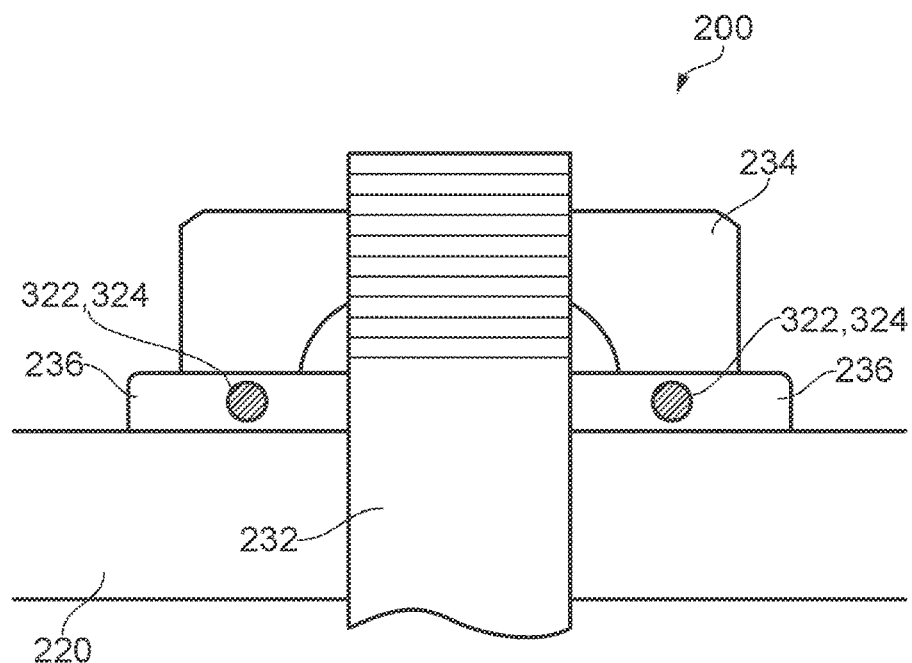
FIG. 8 shows a cross-sectional view of an optical fibre sensor measurement device according to another embodiment of the invention.
Figure 9A:
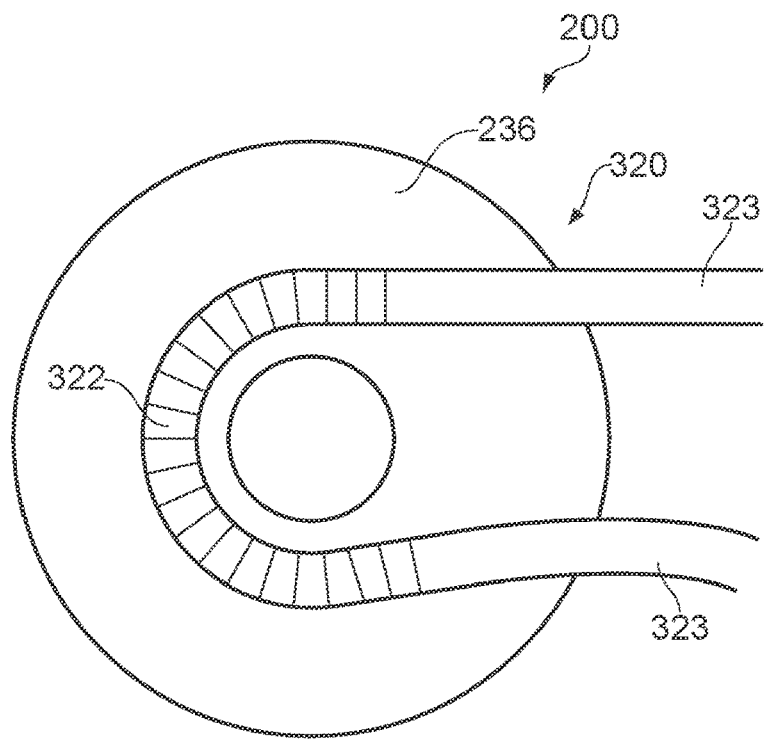
FIGS. 9A-C show plan views of the modified washer of the device of FIG. 8 with different optical fibre sensor configurations.
Figure 9B:
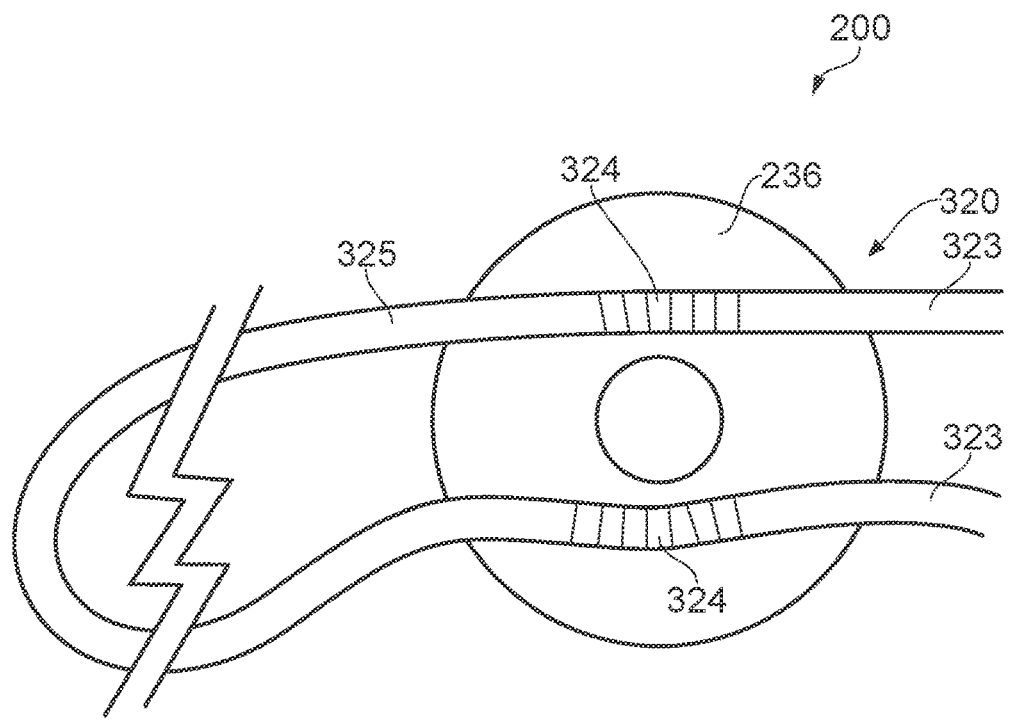
Figure 9C:
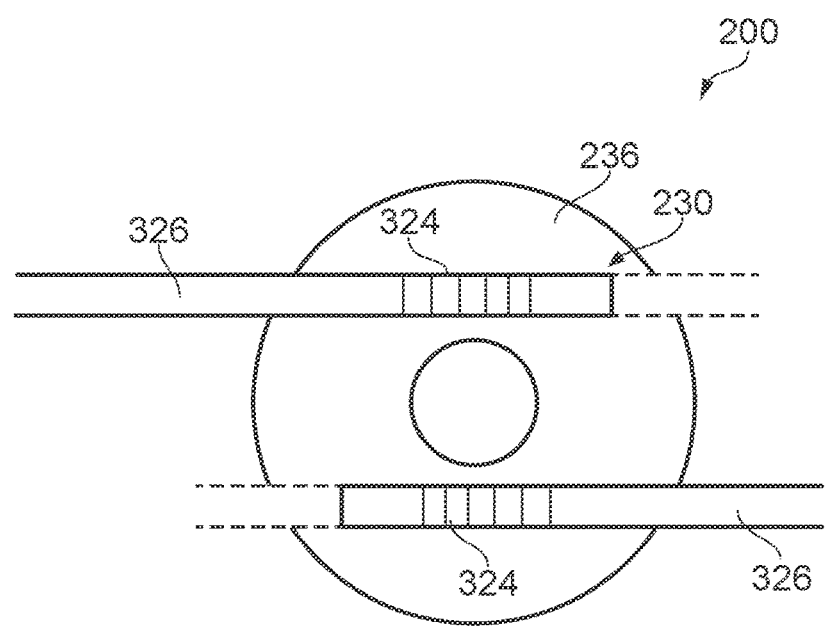

In the embodiment of FIGS. 8 and 9A-C the fibre optic sensor 320 is instead integrated into a modified washer 236, in order to enable the fibre optic sensor 320 to measure pressure within the joint. The washer 236 is made from a compressible material so that a pressure rise in the joint in response to a build-up of trapped generated products causes the washer 236 to change shape. The fibre optic sensor 320 can be arranged in a number of different ways, three of which are illustrated in FIGS. 9A-C.

In FIG. 9A the fibre optic sensor 320 is arranged in a U-shaped loop within the washer 236 so that it forms an open ring around the bolt 232 shank. The fibre optic sensor 320 comprises a fibre Bragg grating portion 322 arranged in a U-shaped loop around the bolt 232 shank and two optical fibre portions 323 extending from either end of the fibre Bragg grating portions 322.

In FIG. 9B the fibre optic sensor 320 is also arranged in a loop, but with two fibre Bragg grating portions 324 arranged so they are at opposite sides of the bolt 232 shank. An optical fibre portion 325 between the two fibre Bragg grating portions 324 is arranged in a long loop (of approximately one meter or more, in the present embodiment) which extends beyond the washer 236. The loop is to provide sufficient distance between the fibre Bragg gratings to ensure a clean response and good resolution. The length of separation is typically defined by fibre Bragg grating manufacturers, and such a long separation may not be necessary in all cases. An advantage of having two separate fibre Bragg grating portions 324 is that the two portions 324 can each measure different physical properties. The arrangement of FIG. 9C is similar to that of FIG. 9B, but with the two fibre Bragg grating portions 324 being provided in separate optical fibre portions 326. An advantage of this arrangement over the FIG. 9B arrangement is that it may be easier to manufacture.

Each fibre Bragg grating portion 322, 324 changes shape in tandem with the washer 236, the strain induced in the fibre Bragg grating portion 322, 234 being measurable. The induced strain causes a change in the wavelength of light that is transmitted through the fibre Bragg grating 322, 324 into the optical fibre portion 323, 325, 326 of the fibre optic sensor 320. This can be detected and calibration factors used to determine a sensed pressure. Thus, the fibre optic sensor 320 is able to measure a change in pressure at the joint over time.

The fibre optic sensor 310 of FIG. 7 and the fibre optic sensor 320 of FIGS. 8 and 9A-C may be incorporated into the same joint, in order to measure multiple properties or effects of trapped generated products. Either sensor 310, 320 may be modified to measure other physical properties, such as temperature or light emission. For measurement of such physical properties it may not be necessary for the modified washer 236 of sensor 320 to be made from a compressible material.

In use, the measurement device 310, 320 of FIGS. 7 to 9 may be installed within a joint 200 as illustrated, and the joint then subjected to one or more simulated lightning strikes. The simulated lightning strike may comprise a simulated direct attachment in which a current representative of a lightning strike is applied directly to the bolt 232 head of the fastener 230 (i.e. the exposed part of the fastener 230 at the exterior surface of the panel 210) or a simulated conducted current in which a current representative of a lightning strike is applied elsewhere within the joint 200, and the current is conducted through the joint 200 to the fastener 230. The appropriate peak current for the representative current depends on the location of the fastener 230 (e.g. its location on the aircraft). The current may also be altered to simulate a range of threat levels to evaluate trends and thresholds. In other embodiments the joint 200 may be subjected to a current representative of another electrical current threat. Such a threat may be, for example, posed by an electrical short circuit between an electrical system and surrounding aircraft structure. The characteristics of such an electrical current threat will be different to that of a lightning strike.

In the event of the simulated lightning strike (or other representative current) generating products (gas, plasma and/or particles) that are trapped within the joint 200, the fibre optic sensor 310, 320 then measures physical properties of those trapped products or the effect of such products on the joint 200. For example, the sensor 310 may provide information about the pressure of generated products trapped at the interface between the bolt 232 shank and the stiffening member 220, and the change in that pressure over time following the strike, while the sensor 320 may provide information about the pressure caused by the trapped products at the interface between the nut 234 and the stiffening member 220. For example, pressure measurements taken by sensor 320 may be used to determine a necessary torque for fastening the fastener 230 of the joint 200.

The measured data from the sensors 310, 320 may then be used to analyse the physical processes at work during the lightning strike (or other representative current) event. Alternatively, or in addition, the measured data may be used to determine whether the joint provides an acceptable fuel ignition threat. This information may be used to inform the design of future joints, as discussed further below.

The measurement devices of FIGS. 2 to 9 may be used in a test programme to provide data about the influence of design features of the joint 200 on the severity of a threat to the joint in response to a simulated lightning strike. The threat may include an ignition source threat and/or a structural integrity threat. Other test programme embodiments may provide such data in respect of other electrical current threats, such as a threat due to an electrical short circuit between an electrical system and aircraft structure.

The design of structural joints is typically dominated by structural considerations such as the load to be transferred through the joint, and the ability of the joint to withstand fatigue. Thus, a fastened joint may have many differing design features, such as the type of material used to manufacture the fastened structural parts (such as panel 210 and stiffening member 220), the thickness of the structural parts, the size and material of the fastener 230, the torque used to fasten the fastener, and the degree of clearance or interference between the fastener and the structural parts. Such design features also contribute to lightning protection, and are influenced by lightning protection requirements. In addition, joints where protection against lightning strike is required often include protection measures such as a layer of metallic mesh at the surface of an exterior panel (such as panel 210) or a spark-suppression cap providing a sealed cavity over the protruding end of a fastener (such as the tail end of fastener 230 that protrudes from the stiffening member 220), and the design features of such protection measures must be specified. Design features may also include manufacturing process specifications, such as dimensional tolerances or surface finishes.

Thus, there is a need for a method to determine a set of design rules, or guidelines, to aid structural designers in specifying such design features in order to provide sufficient, but not excessive, lightning strike protection.

The method of the present embodiment comprises manufacturing a plurality of test assemblies each representative of an identical joint, but with one design feature of that joint modified for each test assembly. For example, for a joint such as joint 200 shown in FIG. 2, each test assembly may comprise a panel 210 having a different thickness. Alternatively, the fastener 230 of each test assembly may be fastened to a different torque level.

Each test assembly is then subjected to one or more simulated lightning strikes. The simulated lightning strike may comprise a simulated direct attachment in which a current representative of a lightning strike is applied directly to the bolt 232 head of the fastener 230 (i.e. the exposed part of the fastener 230 at the exterior surface of the panel 210) or a simulated conducted current in which a current representative of a lightning strike is applied elsewhere within the joint 200, and the current is conducted through the joint 200 to the fastener 230.

The physical properties of the out-gassing products released from the joint 200 in response to an out-gassing event caused by the simulated lightning strike, and/or the physical properties of the joint 200 or containment member 10 influenced by such released out-gassing products, are contained and measured using the device 100 of FIGS. 2 to 6. Alternatively, or in addition, the physical properties of generated products trapped within the joint 200, and/or the physical properties of the joint 200 influenced by such trapped products, are measured using the devices 310, 320 of FIGS. 7 to 9.

The data from measured physical properties, and their changes over time following the simulated strike, are then analysed to determine which of the test assemblies provide an acceptable fuel ignition threat. This data is then used to provide a sensitivity analysis which correlates the fuel ignition threat with the nature of the particular design feature analysed. This sensitivity analysis can then be used to provide a set of design rules for that design feature, i.e. a set of parameters which the design feature must conform to in order to ensure no fuel ignition threat, or an acceptably low threat.

In addition to providing a set of design rules, the sensitivity analysis may also be used to support a new means of qualifying materials and joint types. There is also the potential to optimise a test matrix, which leads to cost savings and lead time reductions.

Some design rules may be interdependent with one another. For example, the density of a metallic mesh provided on the surface of a panel 210 may be interdependent on the acceptable range for the thickness of that panel 210. The design rules may therefore be compiled to provide a model in which at least some of the design rules are interdependent on one another.

In all the above embodiments, or variations thereof, the applied current may be representative of an electrical threat other than a lightning strike. For example, an electrical threat caused by malfunctioning electrical equipment on the aircraft.

Although the invention has been described above with reference to one or more preferred embodiments, it will be appreciated that various changes or modifications may be made without departing from the scope of the invention as defined in the appended claims.

The invention claimed is:

1. A device configured for measuring one or more physical properties of, and/or induced by, gases, plasma and/or particles released from a joint in response to an electrical current threat, the joint comprising a fastener passing through a structure so that an end of the fastener protrudes from the structure, the device comprising:
   a containment member having a base surrounding an opening into a cavity, the containment member being arranged to be mounted over the end of the fastener to enclose the end of the fastener within the cavity and to seal the opening; and
   one or more sensors configured to measure: one or more physical properties of electrically induced gases, plasma and/or particles contained by the cavity; and/or one or more physical properties of the containment member induced by gases, plasma and/or particles contained by the cavity.

2. A device according to claim 1, wherein the one or more sensors comprise: a pressure sensor in fluid communication with the cavity and arranged to measure a pressure within the cavity; a temperature gauge arranged to measure a temperature or temperature distribution of the containment member; and/or a light sensor arranged to measure a light emitted within the cavity.

3. Apparatus for measuring one or more physical properties of, and/or induced by, gases, plasma and/or particles released from a joint in response to an electrical current threat, the apparatus comprising:
   a joint comprising a fastener passing through a structure so that an end of the fastener protrudes from the structure;
   a device according to claim 1; and
   means for delivering an electrical current representative of the electrical current threat to the fastener,
   wherein the containment member of the device is installed over the end of the fastener so as to enclose the end of the fastener within the cavity and to seal the opening.

4. Apparatus according to claim 3, comprising a recording device arranged to record changes in the measured one or more physical properties over time.

5. Apparatus according to claim 3, wherein the joint comprises a test assembly representative of a joint of an aircraft fuel tank.

6. A method of measuring one or more physical properties of, and/or induced by, gases, plasma and/or particles released from a joint in response to an electrical current threat, the joint comprising a fastener passing through a structure so that an end of the fastener protrudes from the structure, the method including the steps of:
   enclosing the end of the fastener within the cavity of a device according to claim 1 and sealing the opening;
   delivering an electrical current representative of the electrical current threat to the fastener; and
   measuring: one or more physical properties of gases, plasma and/or particles released from the joint in response to the applied current and contained within the sealed cavity; and/or one or more physical properties of the containment member induced by the gases, plasma and/or particles.

7. A method according to claim 6, wherein the measuring step includes measuring changes in the one or more physical properties over time.

8. A method according to claim 6, wherein the one or more physical properties includes: a pressure within the sealed cavity; a temperature or temperature distribution of the containment member; a light emitted within the sealed cavity; and/or a material distribution of gases, plasma and/or particles contained within the sealed cavity.

9. A method according to claim 6, wherein the joint comprises a test assembly representative of a joint of an aircraft fuel tank.

10. A method according to claim 9, wherein the sealed cavity is representative of a sealed cavity of a cap enclosing an end of a fastener at the joint of the aircraft fuel tank.

11. A device configured for measuring one or more physical properties of, and/or induced by, gases, plasma and/or particles released from a joint in response to an electrical current threat, the joint comprising a fastener passing through a structure so that an end of the fastener protrudes from the structure, the device comprising:
   a containment member having a base surrounding an opening into a cavity, the containment member being arranged to be mounted over the end of the fastener to enclose the end of the fastener within the cavity and to seal the opening; and
   one or more sensors embedded in the containment member to measure: one or more physical properties of gases, plasma and/or particles contained by the cavity; and/or one or more physical properties of the containment member induced by gases, plasma and/or particles contained by the cavity.

12. The device of claim 11, wherein the containment member comprises one or more channels each configured to receive one of the sensors therewithin.

* * * * *